United States Patent [19]

Schwander et al.

[11] 4,260,770
[45] Apr. 7, 1981

[54] NAPHTHOLACTAM DYES

[75] Inventors: Hansrudolf Schwander, Riehen; Christian Zickendraht, Binningen, both of Switzerland

[73] Assignee: Ciba-Geigy Aktiengesellschaft, Leverkusen, Fed. Rep. of Germany

[21] Appl. No.: 793,094

[22] Filed: May 2, 1977

[30] Foreign Application Priority Data

Jun. 1, 1976 [CH] Switzerland .................. 6864/76

[51] Int. Cl.³ .................. C07D 263/56; C07D 277/64; C07D 235/14
[52] U.S. Cl. .................. 548/159; 548/217; 548/327
[58] Field of Search .......... 260/304 R, 326.27, 304 T, 260/307 D; 548/327, 159, 217

[56] References Cited

U.S. PATENT DOCUMENTS

| | | | |
|---|---|---|---|
| 3,025,294 | 3/1962 | Huebner et al. | 260/326.27 |
| 3,278,551 | 10/1966 | Kleiner et al. | 260/326.27 |
| 3,287,465 | 11/1966 | Brack et al. | 260/305 |
| 3,290,280 | 12/1966 | Voltz et al. | 260/305 |

*Primary Examiner*—Donald G. Daus
*Assistant Examiner*—D. B. Springer
*Attorney, Agent, or Firm*—Sprung, Felfe, Horn, Lynch & Kramer

[57] ABSTRACT

New Dyes of the formula

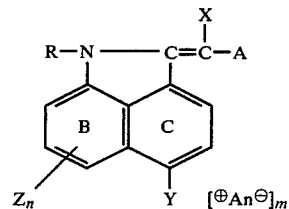

are described wherein
R represents alkyl, alkenyl or preferably hydrogen,
X represents a modified carboxyl group, the radical $-SO_2-T$ or a heterocyclic radical wherein T represents alkyl, alkenyl or preferably aryl,
An represents an anion,
Y represents a basic radical bound by way of a modified carboxyl group,
Z represents a nonionic substituent,
n represents 0, 1 or 2,
m represents 0 or 1,
A represents a heterocyclic radical or $-CN$,
and B and C can carry further nonionic substituents, which dyes yield briliant, bright orange to red dyeings which for the most part fluoresce in ultraviolet light and have excellent fastness properties in service.

6 Claims, No Drawings

NAPHTHOLACTAM DYES

The invention relates to naphtholactam dyes of the general formula (I)

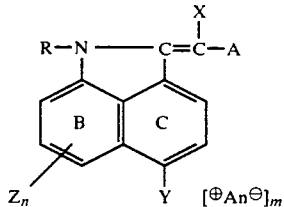 (I)

wherein
R represents alkyl, alkenyl or preferably hydrogen,
X represents a modified carboxyl group, the radical —$SO_2$—T or a heterocyclic radical wherein T represents alkyl, alkenyl or preferably aryl,
An represents an anion,
Y represents a basic radical bound by way of a modified carboxyl group,
Z represents a nonionic substituent,
n represents 0, 1 or 2,
m represents 0 or 1, and
A represents a heterocyclic radical or —CN,
and B and C can carry further nonionic substituents.
The new dyes of the formula (I) can be produced by means of various processes.

A particularly advantageous process comprises condensing a naphtholactam compound of the formula (II)

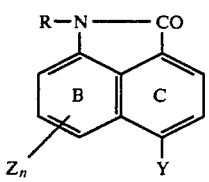 (II)

in the presence of an acid condensation agent, preferably phosphorus oxychloride, with a methylene-active compound of the formula (III)

X—$CH_2$—A    (III), in which formulae the symbols R, X, Y, Z, A, B, C and n have the aforegiven meanings; and, optionally, subsequently treating the resulting condensation product with alkylating agents.

Another of these processes comprises condensing a compound of the formula (IV)

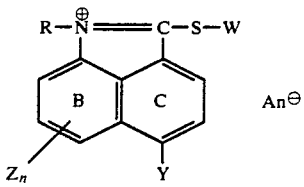 (IV)

wherein W represents a $C_1$-$C_4$-alkyl radical, preferably methyl or ethyl, "An" represents an anion, and R, Z, Y, B, C and n have the aforementioned meanings, with a compound of the formula (III) with the splitting-off of W-SH and H-An; and, optionally, treating the resulting condensation product with alkylating agents.

Preferred dyes of the formula (I) are those wherein X represents —CO—$OR_1$, —CO—Q, —$SO_2$—T, a heterocycle or preferably —CN, whereby $R_1$ represents optionally substituted alkenyl, cycloalkyl, aralkyl, aryl or preferably alkyl, T has the meaning already defined and Q represents the radical of an amine of the formula Q-H; Y represents —CN, —COCl, —CO—Q' or preferably —CO—$OR_1'$, whereby Q' represents the radical of an amine H-Q', and $R_1'$ represents optionally substituted alkyl, alkenyl, cycloalkyl, aralkyl or aryl or a heterocyclic radical; Z represents bromine, chlorine or hydrogen; and A and R have the meaning already defined.

The radical A is preferably an heterocycle of the formula

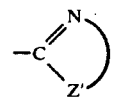

wherein Z' represents the members required to complete a heterocyclic 5- or 6-membered ring which can also contain fused-on aromatic rings, and wherein the rings can contain nonionic substituents.

Particularly preferred dyes are derived from the reactive derivatives of benzimidazole, benzoxazole, benzthiazole, pyridine, quinoline, phenanthridine, indolenine, thiadiazole, triazole, pyrimidine and isoquinoline.

X preferably represents cyanogen and, if it represents a heterocycle, e.g. likewise the group of the formula

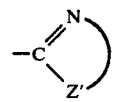

wherein Z' represents the residue to complete a 5- or 6-membered heterocyclic ring which can carry benzo radicals and/or other substituents.

If X represents the carbonamide group —SO—$NR_1'R_2'$ or the ester group —CO—$OR_3'$, the groups $R_1'$, $R_2'$ and $R_3'$ can represent, e.g., the following: $C_1$-$C_{18}$-alkyl groups which are optionally substituted by $C_1$-$C_4$-alkoxy, hydroxy, chlorine, bromine, cyanogen, carboxyl, carb-$C_1$-$C_4$-alkoxy, sulpho, carbonamide or acetoxy; there may be mentioned for example: methyl, butyl, propyl, ethyl, octyl, β-cyanoethyl, β-chloroethyl, β-hydroxyethyl, β-hydroxypropyl, β-hydroxy-γ-chloropropyl, β-carboxyethyl, β-carbomethoxy-, β-carboethoxy- or β-carbobutoxyethyl, β-carbonamidoethyl and β-acetoxyethyl, cycloaliphatic groups such as cyclopentyl, preferably cyclohexyl; phenyl, benzyl or phenethyl optionally substituted by $C_1$-$C_4$-alkyl such as methyl, lower alkoxy such as methoxy, or halogen such as chlorine, or nitro.

The following in particular may be mentioned as radicals Y:
1. Radicals Y of the formula

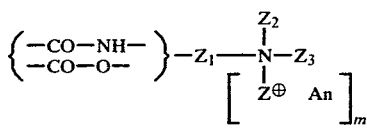

wherein $Z_1$ represents alkyl having 1 to 8 C atoms, preferably 2 to 6 C atoms, or $C_2$-$C_6$-alkylene-(O-$C_2$-$C_6$-alkylene)$_{1-3}$, $Z_2$ represents hydrogen, alkyl, alkenyl or cyloalkyl, $Z_3$ represents hydrogen, alkyl, alkenyl or cycloalkyl, Z represents hydrogen, alkyl, alkenyl, cycloalkyl or aralkyl, and m represents 0 or 1.

Such radicals are, e.g.: —CO—NH—$(CH_2)_{1-4}$—N(-lower alkyl)$_2$, such as dimethylaminoethylamino, dibutylaminoethylamino,

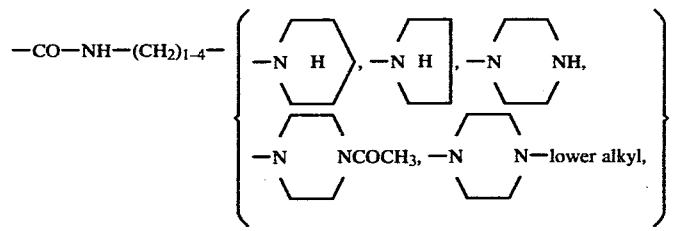

$Z_2$ and $Z_3$ independently of one another represent for example hydrogen, lower alkenyl having 3 to 5 carbon atoms, alkyl having 1 to 6 carbon atoms which can be substituted by carboalkoxy having 1 to 6 carbon atoms or by alkoxy having 1 to 6 carbon atoms.

Z represents, e.g., hydrogen, lower alkenyl having 3 to 5 carbon atoms, alkyl having 1 to 6 carbon atoms which can be substituted by carboalkoxy having 1 to 6 carbon atoms or by alkoxy having 1 to 6 carbon atoms, cyclohexyl or benzyl.

The anionic radicals $An^\ominus$ can be both inorganic ions and organic ions; to be mentioned are for example: chloride, bromide, iodide, $CH_3SO_4^\ominus$, $C_2H_5SO_4^\ominus$, p-toluenesulphonate, $CH_3SO_3^\ominus$, $HSO_4^\ominus$, benzenesulphonate, p-chlorobenzenesulphonate, phosphate, acetate, formiate, propionate, oxalate, lactate, maleinate, crotonate, tartrate, zitrate, $NO_3^\ominus$, perchlorate and $ZnCl_3^\ominus$.

Among the anions, the halides such as chloride, bromide and iodide, hydrogen sulphate, sulphate, phosphate and methosulphate have particular importance since they occur directly in the production of the new dyes. The dyes thus obtained can be converted by known exchange reactions into other dyes containing anions. The nature of the anionic radicals is of no consequence with regard to the application of the dyes, provided that largely colourless radicals are concerned which do not affect the solubility of the dyes in an undesirable manner.

Suitable alkyl radicals are methyl, ethyl, n-propyl, isopropyl, n-butyl, iso-butyl, 2-methyl-propyl-1, iso-amyl as well as substitution products thereof, such as β-chloroethyl and β-cyanoethyl.

It is also possible to introduce the group —$NZ_1Z_3Z^\oplus$... $An^\ominus$ by reacting dyes in which Y represents a group of the formula —CO—(NH or O)—$Z_1$—Hal with a compound of the formula $NZ_2Z_3Z$ wherein $Z_1$, $Z_2$, $Z_3$ and Z have the aforegiven meanings, and "Hal" represents a mobile halogen atom (bromine, chlorine) or an anion of sulphuric acid or of a sulphonic acid.

Suitable amines $NZZ_2Z_3$ are, e.g., trimethyl- or triethylamine or pyridine, that is, preferably low-molecular, optionally substituted alkylamines or aralkylamines; besides the already mentioned trimethyl- or triethylamine, e.g. also tripropylamine, tributylamine, trihydroxyethylamine, dimethylhydroxyethylamine, monomethylmonoethylhydroxyethylamine, etc. But also those amines containing alkyl radicals differing from each other can be used, such as monomethyldiethylamine, monomethyldipropylamine, etc. Two or three of the radicals $R_1$, $R_2$ and $R_3$ can form with the tertiary N atom a saturated or unsaturated heterocyclic ring system, such as a pyridine ring or compounds of the formulae

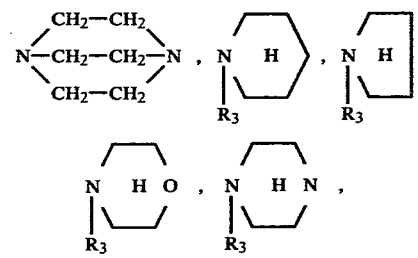

wherein $R_3$ represents the amino group or an optionally substituted, low-molecular alkyl group.

In place of the amines $NZZ_2Z_3$, applicable, completely alkylated diamines are, e.g.: 1,2-bis(dimethylamino)ethane, 1,3-bis(dimethylamino)propane, 1,3-bis(dimethylamino)propene, 1,2-bis(dimethylamino)propane, 1,4-bis(dimethylamino)butane, 1,3-bis(dimethylamino)butane, 1,3-bis-dimethylamino-2-methylpropane, 2,3-bis(dimethylamino)butane, 1,5-bis-dimethylamino-2-pentene, 1,5-bis(dimethylamino)pentane, 2,3-bis-dimethylamino-2-methylbutane, 1,6-bis(dimethylamino)hexane, 1,7-bis(dimethylamino)heptane, 3,4-bis-dimethylamino-3,4-dimethylhexane, 1,10-bis(dimethylamino)decane, 1,12-bis(dimethylamino)dodecane, 1-dimethylamino-2-diethylamino-ethane, 1-dimethylamino-2-(dimethylaminomethyl)butane, 1,2-bis(diethylamino)ethane, 1,3-bis(diethylamino)propane, 4-dimethylamino-1-diethylaminopentane, 1,4-bis(dimethylamino)1,3-butadiene, 1,3-bis(diethylamino)1-butane, 1-dimethylamino-2-(isopropylpentylamino)-ethane, 1-dimethylamino-2-(methylheptylamino)-ethane, bis-(dialkylamino)-methane, 1-dimethylamino-2-(alkylhexylamino)-ethane, 1-dimethylamino-2-(methyloctylamino)-ethane, 1-dimethylamino-2-(butyloctylamino)-ethane, 1,4-bis-(diisopropylamino)-2-butene, 1,16-bis-(dimethylamino)-hexadecane, 1-dimethylamino-2-(methylpentadecylamino)-ethane.

Triamines and tetramines which can be used are, e.g.: methyl-bis-(2-dimethylaminoethyl)-amine or ethyl-bis-(2-diethylaminoethyl)-amine.

Radicals

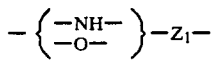

bound in the radical Y to the carbonyl group are, e.g.:

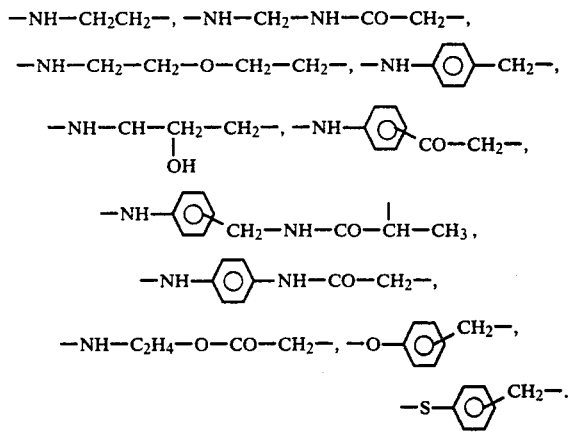

2. Radicals Y of the formula

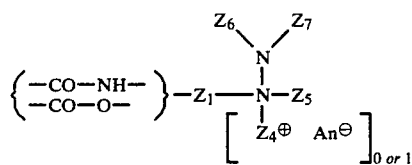

wherein An and $Z_1$ have the aforegiven meanings, $Z_4$ represents an optionaly substituted alkyl, cycloalkyl or aralkyl radical, or together with $Z_5$ and the adjacent N atom, or together with the bridge member $Z_1$ and the adjacent N atom, a heterocyclic ring system, $Z_5$ represents an optionally substituted alkyl, cycloalkyl or aralkyl radical, or together with $Z_4$ and the adjacent N atom a heterocyclic ring system, $Z_6$ and $Z_7$ represent hydrogen or optionally substituted alkyl, cycloalkyl or aralkyl radicals which are identical or different from each other, or acyl radicals which are identical or different from each other, or whereby $Z_4$ and $Z_5$ together with $Z_6$ and $Z_7$ respectively and N atoms adjacent to these substituents can form a saturated or unsaturated 5- or 6-membered heterocyclic ring, and preferably rings wherein $Z_6$ and $Z_7$ represent hydrogen or optionally substituted alkyl, cycloalkyl or aralkyl which are identical or different from each other, or acyl radicals which are identical or different from each other.

The hydrazine compounds can also be obtained by treating dyes containing the aforementioned group —CO—(NH— or —O)—$Z_1$—Hal with hydrazines.

Hydrazines which can be used are preferably those which carry two hydrocarbon radicals bound on the same nitrogen atom, inter alia the optionaly further substituted N,N-dialkylhydrazines, e.g. N,N-dimethyl-, N,N-diethyl-, N,N-di-n-propyl-, N,N-di-isopropyl-, N,N-di-n-butyl-, N-methyl-N-ethyl-, N-methyl-N-n-propyl-, N-methyl-N-n-butyl-, N-ethyl-N-n-propyl-, N-ethyl-N-isopropyl-, N-methyl-N-β-hydroxyethyl-, N-ethyl-N-β-hydroxyethyl-, N-methyl-N-β-hydroxypropyl-, N-methyl-N-γ-hydroxypropyl-, N,N-di-(β-hydroxyethyl)-, N,N-di-(β-hydroxypropyl)-hydrazine; the optionally further substituted N-alkyl-N-aryl-hydrazines, e.g. N-methyl-N-phenyl-, N-methyl-N-4'-methylphenyl-, N-ethyl-N-phenyl-, N-β-hydroxyethyl-N-phenylhydrazine; the optionally further substituted N-alkyl-N-cycloalkylhydrazines, e.g. N-methyl-N-cyclohexyl-, N-ethyl-N-cyclohexyl-, N-methyl-N-4'-methylcyclohexyl-, N-β-hydroxyethyl-N-cyclohexylhydrazine; as well as the N,N-di-cyclohexylhydrazine as an example of an N,N-dicycloalkylhydrazine; the optionally further substituted N-alkyl-N-aralkylhydrazines, e.g. N-methyl-N-benzyl-, N-ethyl-N-benzyl-, N-β-hydroxyethyl-N-benzyl-, N-methyl-N-phenylethyl-, N-ethyl-N-phenylethyl-, N-β-hydroxyethyl-N-phenylethyl-hydrazine, as well as the N,N-dimethyl- and N,N-di-(phenylethyl)-hydrazines as examples of N,N-di-aralkylhydrazines; but also the optionally further substituted tri- or tetraalkylhydrazines, e.g. N,N,N'-trimethyl-, N,N,N'-triethyl-, N,N-dimethyl-N'-ethyl-, N,N-diethyl-N'-methyl-, N-methyl-N,N'-diethyl-, N-ethyl-N,N'-dimethyl-, N,N-dimethyl-N'-n-propyl-, N,N-dimethyl-N'-n-butyl-, N,N-dimethyl-N'-β-hydroxyethyl-, N,N-diethyl-N'-β-hydroxyethyl-, N,N,N',N'-tetramethyl-, N,N,N',N'-tetraethyl-, N,N-dimethyl-N',N'-diethyl-, N,N,di-methyl-N',N'-di-(β-hydroxyethyl)-, N,N-dimethyl-N',N'-di-n-propylhydrazine; also N,N-dimethyl-N'-phenyl-, N,N-dimethyl-N'-benzyl-, N,N-dimethyl-N'-phenylethyl-, N,N-dimethyl-N'-cyclohexyl-, N,N,N'-trimethyl-N'-phenyl-, N,N,N'-trimethyl-N'-benzylhydrazines as well as N-aminopiperidines, N-methylaminopiperidine, N-dimethylaminopiperidine, N-aminomorpholine, N-aminopyrrolidine, N-methylaminomorpholine or N-dimethylaminomorpholine. Particularly preferably is used the N,N-dimethylhydrazine (asymmetrical dimethylhydrazine) of the formula

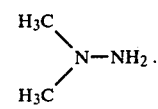

Acyl radicals $R_3$ or $R_4$ are preferably those of the formula $R_6$—$SO_2$— or $R_6$—CO—, wherein $R_6$ represents hydrogen or an aromatic radical or a saturated or unsaturated aliphatic or cycloaliphatic radical, which together with $R_4$ and N can form a ring, $R_3$ or $R_4$ can represent, e.g., formyl, acetyl, propionyl, butyroyl, acryloyl, cyanacetyl, benzoyl, dimethylaminoacetyl, methylsulphonyl or optionally substituted phenylsulphonyl; $R_3$ and $R_4$ together can represent, e.g., optionally substituted succinoyl, maleinoyl or phthaloyl.

3. Radicals Y of the formula

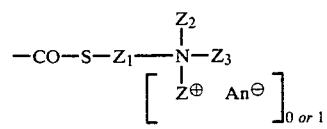

wherein An, Z, $Z_1$, $Z_2$ and $Z_3$ have the meanings defined in the foregoing.

4. Radicals Y of the formulae

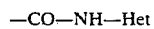

and

—CO—O—Het wherein "Het" represents a group containing a basic heterocycle, whereby the heterocycle is bound either (a) directly or (b) by way of an intermediate member to the O atom or the NH group. The radical "Het" is optionally quaternised.

4.(a) Suitable radicals "Het" are, e.g., those of the formulae

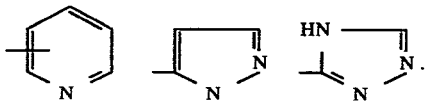

4.(b) Suitable radicals in which the heterocyclic radical is bound by way of a bridge member to the carbonyl group are, e.g.,

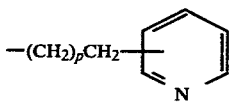

wherein p=0, 1, 2, 3, 4 or 5,

—$(CH_2)_p$—$CH_2$—$A_1$.

wherein $A_1$ represents the radical of an azole or of an azolium compound, for which, e.g., the above-defined radical of the formula

is applicable.

Radicals R are, besides hydrogen, in particular alkyl having 1 to 8 carbon atoms, hydroxyalkyl having 2 or 3 carbon atoms, alkoxyalkyl having 3 to 8 carbon atoms, β-chloroethyl, β-cyanoethyl, alkoxycarbonylethyl having 1 to 4 carbon atoms in the alkoxy, carbamoylethyl, N-mono- or N,N-disubstituted alkylcarbamoylethyl having 1 to 4 carbon atoms in the alkyl group, cyclohexyl, benzyl, phenylethyl or phenyl, also alkenyl. The aliphatic groups and hydrogen are preferred.

Individually there may be mentioned for example: propyl, butyl, hexyl, β-ethylhexyl, β-hydroxyethyl or β-hydroxypropyl, methoxyethyl, ethoxyethyl, methoxypropyl, ethoxypropyl, butoxypropyl, amyloxypropyl, methoxycarbonylethyl, ethoxycarbonylethyl, allyl or butoxycarbonyl ethyl and, preferably, methyl, ethyl, benzyl and in particular hydrogen.

The expression "lower" indicates, when it is used in connection with definitions such as alkyl, alkoxy, carbalkoxy, etc., that the alkyl groups occurring in the radical contain no more than 4 carbon atoms.

Examples of nonionic substituents Z on the rings B and C are alkyl, alkoxy, halogen, nitro, alkylmercapto, alkylsulphonyl, arylsulphonyl, acylamino, cyano, carbonamide and sulphonamide, and by alkyl are meant especially those having 1 to 4 carbon atoms, such as methyl, ethyl, isopropyl and n-butyl; by alkoxy groups are meant in particular those having 1 to 4 carbon atoms, such as methoxy, ethoxy, n-propoxy, n-butoxy and isopropoxy; by halogen are meant, besides fluorine, particularly chlorine and bromine; by alkylmercapto and alkylsulphonyl are meant especially those having 1 to 4 carbon atoms in the alkyl group, such as methyl-, β-hydroxy-ethyl-, isopropyl- or n-butyl-mercapto or -sulphonyl; by arylsulphonyl is meant particularly phenylsulphonyl; by aralkylsulphonyl is meant preferably benzylsulphonyl; by acylamino is meant especially $C_1$–$C_4$-alkylcarbonylamino, such as acetylamino and $C_1$–$C_4$-alkylsulphonylamino, such as methylsulphonylamino; and by carbonamide and sulphonamide radicals are meant, in particular, carbonamide or sulphonamide radicals substituted by one or two alkyl groups containing 1 to 4 carbon atoms, such as methyl, ethyl or n-butyl.

The reaction of the naphtholactam of the formula (II) with the methylene-active compounds of the formula (III) is performed in the presence of an acid condensation agent, such as phosphorus oxybromide, phosphorus trichloride, phosphorus tribromide, phosphorus pentachloride, thionyl chloride or phosgene (in an autoclave) or mixtures of phosphorus oxychloride and phosphorus pentoxide, especially however in the presence of phosphorus oxychloride.

The reaction is carried out preferentially at elevated temperature, e.g. at temperatures of 50° to 200° C., preferably however within a range of 60° to 130° C. It is advantageously performed in an inert organic solvent such as benzene, toluene, xylene, chlorobenzene, dichlorobenzene, nitrobenzene, ethylene chloride, carbon tetrachloride or chloroform.

The condensation of compounds IV and III is performed under alkaline reaction conditions, advantageously in an organic solvent such as methanol, ethanol, butanol, ethylene glycol monomethyl ether, dimethylformamide, pyridine or chlorobenzene in the presence of a condensation agent reacting alkaline, such as triethylamine, potassium carbonate, sodium hydroxide or magnesium oxide, at elevated temperature, advantageously at 40° to 140° C., preferably at 60° to 100° C.

The starting products of the formula (II) are obtainable in a known manner by reaction of a naphtholactam compound of the formula (IV) with diphosphorus pentasulphide to give the corresponding thione compound, and reaction thereof with quaternising agents R-An, preferably dimethyl sulphate.

A further means of obtaining the dyes of the formula (I) consists of performing the condensation with halogen-containing condensation agents, such as in particular phosphorus oxychloride, in such a manner that in the 4-position of the naphtholactam there is formed a —CO-halogen group, especially a chlorocarbonyl group, which is subsequently reacted with alcohols, phenols, amines or mercaptans to the corresponding esters, amides or thioesters.

Hydroxy compounds suitable for the reaction are, e.g.: aminoalcohols such as 2-aminoethanol, 3-aminopropanol, 1-amino-2-propanol, 2-amino-2-methylpropanol, 2-aminobutanol, 3-aminobutanol, 3-amino-2-butanol, 3-amino-3-methyl-2-butanol, 2-methylaminoethanol, 2-dimethylaminoethanol, 2-ethylaminoethanol, 2-diethylaminoethanol, 3-methylaminopropane, 3-dimethylaminopropanol, 3-ethylaminopropanol, 3-dimethylaminopropanol, 1-methylamino-2-propanol, 1-dimethylamino-2-propanol, 1-ethylamino-2-propanol, 1-diethylamino-2-propanol, 3-methylaminobutanol, 3- dimethylaminobutanol, 3-ethylaminobutanol, 3-diethylaminobutanol, 3-methylamino-2-butanol, 3-dimethylamino-2-butanol, 3-ethylamino-2-butanol, 3-diethylamino-2-butanol, 2-(2-aminoethylamino)-ethanol, N-(2-hydroxyethyl)-piperidine, 2-aminocyclohexanol, 2-methylaminocyclohexanol, 2-dimethylaminocyclohexanol, 2-benzylaminoethanol and α-aminomethylbenzyl alcohol.

Amino compounds suitable for the reaction are, e.g.:

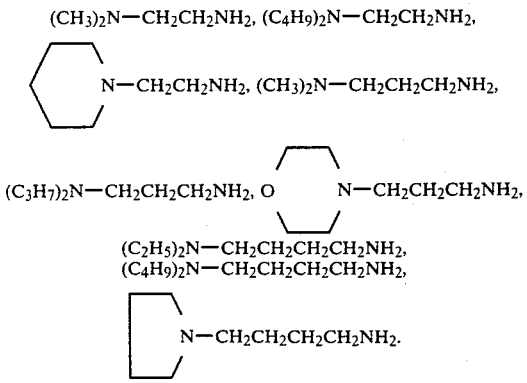

As a rule, the diamines, which however contain no quaternary nitrogen atoms, are reacted in organic media, such as methyl ethyl ketone, acetone, acetonitrile, and others.

The salt-like reaction products are largely insoluble in the above-mentioned media and can be separated by filtration.

The group present in the group Y is advantageously so chosen that, with a pH value of 4 in the aqueous dye bath, at least 60%, preferably at least 80%, of the dye is in the form of salt.

The naphtholactam compounds of the formula (II) used as starting products are obtainable by reacting o-xylylenedicyanide with glyoxal in the presence of a base (NaOH, KOH) and of a solvent at temperatures below 50° C. (e.g. 0° to 40° C.) to give 1,4-dicyanonaphthalene, and subsequently either (a) hydrolysing the 1,4-dicyanonaphthalene in a basic or preferably acid medium to 1,4-dicarboxylic acid, either converting the 1,4-naphthalenedicarboxylic acid into a functional derivative and then converting this with a 10 to 50% excess of nitric acid to the 8-nitro-1,4-naphthalenedicarboxylic acid derivative and reducing this to the 8-amino derivative, or nitrating directly the 1,4-dicarboxylic acid and subsequently reducing the nitrated product to 8-aminonaphthalene-1,4-dicarboxylic acid, and then converting the 8-amino derivative either by spontaneous ring closure or by heating into 1,8-naphtholactam-4-carboxylic acid or into functional derivatives thereof; or (b) nitrating the 1,4-dicyanonaphthalene with a 10 to 50% excess of nitric acid in the 8-position and subsequently reducing the nitro group to the 8-amino group, bringing about the naphtholactam ring closure by spontaneous formation or by heating, and hydrolysing the cyanogen group in the 4-position, if it has not already been hydrolysed with the reduction of the 8-nitro group, optionally by way of the stage of 4-carboamido-1,8-naphtholactam in a basic or acid medium.

The naphtholactams, which carry on the lactam ring as substituent R an organic group, are obtained, e.g., by alkylating the corresponding naphtholactams, which carry on the nitrogen atom of the lactam ring hydrogen (R=H), in a polar aprotic solvent, such as dimethylformamide or N-methylpyrrolidone, with a toluenesulphonic acid ester of the formula

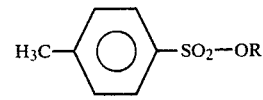

in the presence of a strong base, such as sodium or potassium hydroxide. R represents the same as above.

Alkylating and quaternising agents are, for example: esters of strong mineral acids, particularly low-molecular sulphuric acid esters, or organic sulphonic acids, for example dimethylsulphate, diethylsulphate, alkyl halides, e.g. methyl chloride, methyl bromide or methyl iodide, aralkyl halides, e.g. benzyl chloride, esters of low-molecular alkanesulphonic acids, i.e. those containing 1 to 4 C atoms, such as methyl esters of methane-, ethane- or butanesulphonic acid, and esters of benzenesulphonic acids, such as the methyl, ethyl, propyl or butyl esters of benzenesulphonic acid, of 2- or 4-methylbenzenesulphonic acid, 4-chlorobenzenesulphonic acid or 3- or 4-nitrobenzenesulphonic acid.

Preferred methylene-active starting compounds of the formula III are the azoleacetic acid derivatives of the formula

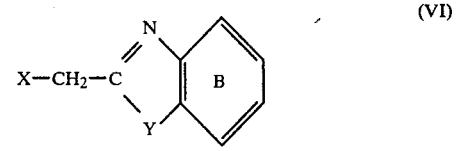

wherein Y represents an —S— or —O— atom or an —NR''— group, and the ring B can carry nonionic substituents or optionally substituted, annularly-linked rings, with suitable substituents for the ring B being, for example, one or more halogen atoms, among which are meant here in general particularly chlorine or bromine atoms, lower-alkoxy groups (e.g. methoxy, ethoxy, propoxy and butoxy groups), and hydroxy, cyano, vinyl, nitro, lower-alkylamino, dialkylamino, phenylamino, N-phenyl-N-alkylamino, phenyl, phenoxy, acyl, acyloxy or acylamino groups. Particularly preferred are lower alkyl groups, especially unsubstituted methyl and ethyl groups.

The following may be mentioned as examples of suitable compounds of the formula VI:

benzoxazolyl-(2)-acetic acid ester, 5-methyl-benzoxazolyl-(2)-acetic acid methyl ester, 4,5-dimethyl-benzoxazolyl-(2)-acetic acid-n-propyl ester, 5-chlorobenzoxazolyl-(2)-acetic acid ethyl ester, 5-bromobenzoxazolyl-(2)-acetic acid methoxyethyl ester, naphth-[1,2-d]-oxazolyl-(2)-acetic acid ethyl ester, naphth-[2,3-d]-oxazolyl-(2)-acetic acid methyl ester, 5-ethylsulphonylbenzoxazolyl-(2)-acetic acid ethyl ester, benzoxazolyl-(2)-acetamide, 5-methylbenzoxazolyl-(2)-acetamide, 5-chlorobenzoxazolyl-(2)-acetamide, 5-ethylsulphonyl-benzoxazolyl-(2)-acetamide, 5-dimethylaminosulphonyl-benzoxazolyl-(2)-acetamide, 5-methyl-benzoxazolyl-(2)-acetic acid methyl amide, 4,5-dimethylbenzoxazolyl-(2)-acetic acid methyl amide, 5-cyclohexylbenzoxazolyl-(2)-acetic acid cyclohexylamide, 5-phenylbenzoxazolyl-(2)-acetic acid isophorylamide, naphth-[1,2-d]-oxazolyl-(2)-acetic acid methylamide, 5-methoxybenzoxazolyl-(2)-acetic acid n-propylamide, 5-bromobenzoxazolyl-(2)-acetic acid methylamide, 5-benzyl-benzoxazolyl-(2)-acetic acid methylamide, 5-(1′, 1′,3′,3′-tetramethyl-n-butyl)-benzoxazolyl-(2)-acetic acid anilide, 5-phenylsulphonyl-benzoxazolyl-(2)-acetic acid anilide, 5-benzylsulphonyl-benzoxazolyl-(2)-benzoxazolyl-(2)-acetic acid methylamide, 5-diethylaminocarbonyl-benzoxazolyl-(2)-acetic acid n-butylamide, 5-methoxy-benzoxazolyl-(2)-acetic acid cyclohexylamide, 5-ethoxy-benzoxazolyl-(2)-acetic acid anilide, 5-phenoxybenzoxazolyl-(2)-acetic acid anilide, 5-acetylamino-benzoxazolyl-(2)-acetic acid 3′-methoxy-n-propylamide, 5-chlorobenzoxazolyl-(2)-acetic acid methylamide, benzoxazolyl-(2)-acetic acid n-propylamide, 5-methyl-benzoxazolyl-(2)-acetic acid ethylamide, 5-methyl-benzoxazolyl-(2)-acetic acid n-propylamide, 5-methyl-benzoxazolyl-(2)-acetic acid 2′-hydroxyethylamide, 5-methyl-benzoxazolyl-(2)-acetic acid 3′-methoxy-n-propylamide, 5-methyl-benzoxazolyl-(2)-acetic acid 2′-bromoethylamide, 5-methyl-benzoxazolyl-(2)-acetic acid isobutylamide, 5-methyl-benzoxazolyl-(2)-acetic acid n-hexylamide, 5-methyl-benzoxazolyl-(2)-acetic acid benzylamide, 5-methyl-benzoxazolyl-(2)-acetic acid anilide, 5-methyl-benzoxazolyl-(2)-acetic acid dimethylamide, 5-methyl-benzoxazolyl-(2)-acetic acid diethylamide, 5-methyl-benzoxazolyl-(2-acetic acid di-n-butylamide, 5-methyl-benzoxazolyl-(2)-acetic acid aziridide, 5-methyl-benzoxazolyl-(2)-acetic acid pyrrolidide, 5-methyl-benzoxazolyl-(2)-acetic acid piperidide, 5-methyl-benzoxazolyl-(2)-acetic acid piperazide, 5-methyl-benzoxazolyl-(2)-acetic acid morpholide, benzthiazolyl-(2)-acetic acid ethyl ester, 6-methyl-benzthiazolyl-(2)-acetic acid methyl ester, 6-methoxy-benzthiazolyl-(2)-acetic acid n-propyl ester, 6-ethoxybenzthiazolyl-(2)-acetic acid ethyl ester, 6-chlorobenzthiazolyl-(2)-acetic acid methyl ester, naphth-[1,2-d]-thiazolyl-(2)-acetic acid ethyl ester, benzthiazolyl-(2)-acetamide, 6-methylbenzthiazolylo-(2)-acetic acid methylamide, 6-chlorobenzthiazolyl-(2)-acetic acid ethylamide, 6-methoxybenzthiazolyl-(2)-acetic acid morpholide, 6-ethoxy-benzthiazolyl-(2)-acetic acid dimethylamide, bis-benzoxazolyl-methane, bis-(5-methyl-benzoxazolyl)-methane, bis-(5,6-dimethyl-benzoxazolyl)-methane, bis-(5-chlorobenzoxazolyl)-methane, bis-(5-bromobenzoxazolyl)-methane, bis-(5-fluorobenzoxazolyl)-methane, bis-(5-ethylsulphonyl-benzoxazolyl)-methane, bis-(5-tertiarybutyl-benzoxazolyl)-methane, bis-(5-ethyl-benzoxazolyl)-methane, bis-(5-cyclohexyl-benzoxazolyl)-methane, bis-(5-phenyl-benzoxazolyl)-methane, bis-(6-methoxy-benzoxazolyl)-methane, bis-(5-benzylbenzoxazolyl)-methane, bis-(5-dimethylaminosulphonyl-benzoxazolyl)-methane, bis-(5-diethylaminocarbonyl-benzoxazolyl)-methane, bis-(5-ethoxybenzoxazolyl)-methane, bis-(5-phenoxy-benzoxazolyl)-methane, bis-(5-acetylamino-benzoxazolyl)-methane, bis-benzthiazolyl)-methane, bis-(6-methyl-benzthiazolyl)-methane, bis-(6-methoxybenzthiazolyl)-methane, bis-(6-chlorobenzthiazolyl)-methane, benzimidazolyl-5-methyl-benzoxazolyl-methane, benzimidazolylbenzthiazolyl-methane, benzthiazolyl-5-methyl-benzoxazolyl-methane, 5-methyl-benzimidazolyl-2-benzoxazolyl-methane, 1-methyl-benzimidazolyl-5-phenyl-benzoxazolyl-methane, 1β-cyanoethyl-benzimidazolyl-5-cyclohexyl-benzoxazolyl-methane, 1-ethylbenzimidazolyl-5-chlorobenzoxazolyl-methane, 5-methyl-benzoxazolyl-acetamide-6-sulphonic acid, benzthiazolylacetamide-5-sulphonic acid or benzthiazolylacetamide-6-sulphonic acid, bis-(5-methyl-6-sulphobenzoxazolyl)-methane, 5-methylbenzoxazolyl-phenylsulphonyl-methane, benzthiazolyl-phenylsulphonyl-methane, benzthiazolyl-benzylsulphonylmethane, benzthiazolylmethylsulphonylmethane, benzthiazolyl-(p-methylphenyl)-sulphonylmethane, benzoxazolyl-(p-methylphenyl)-sulphonylmethane, benzthiazolyl-(p-chlorophenyl)-sulphonylmethane, benzthiazolyl-(p-methoxy)-sulphonylmethane, benzthiazolyl-(2)-acetamide-6-sulphonic acid, benzoxazolyl-(2)-acetamide-6-sulphonic acid, benzimidazolyl-acetonitrile, methylbenzimidazolylacetonitrile, dimethylbenzimidazolylacetonitrile, chlorobenzimidazolylacetonitrile, nitrobenzimidazolylacetonitrile, ethoxycarbonylbenzimidazolylacetonitrile, cyanobenzimidazolylacetonitrile, naphthimidazolylacetonitrile, benzimidazolylacetic acid esters and benzimidazolylacetic acid amides.

Methylene-active compounds having 2 heterocyclic groups are, for example, those of the formula

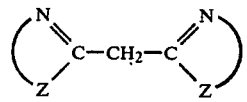

wherein Z has the meaning already defined.

Further valuable heterocyclic methylene-active compounds are, for example, also those of the formulae

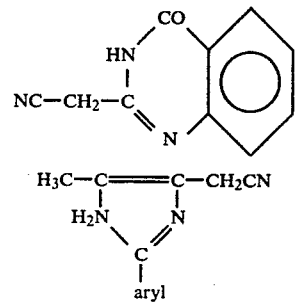

wherein the aryl group is, e.g., a phenyl group or a phenyl group substituted by $C_1$-$C_3$-alkyl or $C_1$-$C_3$-alkoxy; and of the formulae

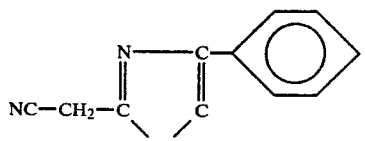

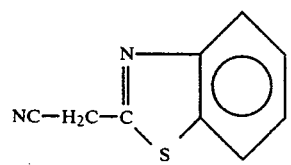

A further preferred group consists of the cyanoacetic acid derivatives, such as cyanoacetic acid $C_1$–$C_5$-alkyl ester, such as $NC-CH_2-CO-O-(CH_3, C_2H_5, C_3H_7$ or $C_4H_9)$, cyanoacetic acid hydrazide, cyanoacetic acid amide and N-alkylated and N-arylated derivatives thereof, 2-cyanoacetanilide, cyanoacetylurea, cyanoacetylurethane such as $NC-CH_2-CO-NH-CO-O(CH_3$ or $C_4H_9)$, ω-cyanoacetophenones such as $NC-CH_2-CO-C_6H_5$ or $NC-CH_2-CO-C_6H_4-COOH(-o)$.

The dyes of the formula (I) yield brilliant, bright orange to red dyeings which for the most part fluoresce in ultraviolet light and have excellent fastness properties in service. If m in the formula (I) represents O, the dyes belong to the class of disperse dyes, with reference being made here to the Colour Index with regard to the dye class.

The unquaternised new dyes are suitable for dyeing semi- and fully-synthetic fibres, such as fibres of polyurethanes, polyacrylonitrile fibres, polyolefins such as basically modified polypropylene, polypropylene modified with nickel and unmodified polypropylene, cellulose triacetate and cellulose $2\frac{1}{2}$ acetate, fibres of polyamides such as nylon 6, nylon 6.6 and nylon 12, and fibres from aromatic polyesters such as those from terephthalic acid and ethylene glycol, or 1,4-dimethylolcyclohexane and mixed polymers from terephthalic and isophthalic acid and ethylene glycol.

The dyeing of the mentioned fibre materials with the said dyes, preferably difficultly soluble in water, is advantageously performed from aqueous dispersion.

It is therefore of advantage to finely divide the representatives usable as disperse dyes by grinding them with textile auxiliaries, such as dispersing agents and possibly grinding agents. On subsequent drying are obtained dye preparations consisting of the textile auxiliary and the dye.

The following may be mentioned as examples of dispersing agents of the nonionic group which can be advantageously used: addition products of 8 moles of ethylene oxide with 1 mole of p-tert.-octylphenol, of 15 or 6 moles of ethylene oxide with castor oil, of 20 moles of ethylene oxide with the alcohol $C_{16}H_{33}OH$, ethylene oxide addition products with di-[α-phenylethyl]-phenols, polyethylene oxide-tert.-dodecyl-thioether, polyamine-polyglycol ether, or addition products of 15 or 30 moles of ethylene oxide with 1 mole of amine $C_{12}H_{25}NH_2$ or $C_{18}H_{37}NH_2$.

Anionic dispersing agents which may be mentioned are: sulphuric acid esters of alcohols of the aliphatic series having 8 to 20 carbon atoms, of the ethylene oxide adducts of the corresponding fatty acid amides, or of alkylated phenols having 8 to 12 carbon atoms in the alkyl group; sulphonic acid esters with alkyl groups having 8 to 20 carbon atoms; sulphating products of unsaturated fats and oils; phosphoric acid esters with alkyl groups having 8 to 20 carbon atoms; fatty acid soaps, also alkylarylsulphonates, condensation products of formaldehyde with naphthalenesulphonic acid and lignin sulphonates.

Suitable cationic dispersing agents are quaternary ammonium compounds which contain alkyl or aralkyl groups having 8 to 20 carbon atoms.

The dye preparations can contain, in addition to the dispersing agents, also organic solvents, particularly solvents boiling above 100° C., which are preferably miscible with water, such as mono- and dialkyl glycol ethers, dioxane, dimethylformamide or dimethylacetamide, tetramethylenesulphone or dimethylsulphoxide. Dye, dispersing agent and solvent are advantageously ground together.

Such a dye preparation is produced, e.g., by mixing to a paste 2 to 30, preferably 5 to 20, percent by weight of the dispersing agent with 10 to 55, preferably about the two- to four-fold amount of dye, and about 10 to 20 parts of a glycol or of another water-retaining agent. The pH value is subsequently adjusted, for example, to about 9 with a dilute acid, preferably with sulphuric acid or acetic acid, and the volume is made up with water to 100%. The mixture is then ground, e.g. in a glass-ball mill or in an other dispersing device to the required degree of fineness, for which purpose the grinding temperature can be between 20° and 90° C.

The dyeing of the polyester fibres with the difficultly water-soluble dyes according to the invention from an aqueous dispersion is performed by the processes customary for polyester materials. Polyesters of aromatic polycarboxylic acids with polyhydric alcohols are dyed preferably at a temperature of above 100° C. under pressure. The dyeing can however also be performed at the boiling point of the dye bath in the presence of dye carriers, for example phenylphenols, polychlorobenzene compounds or similar auxiliaries; or it can be performed by the thermosol process, i.e. padding with subsequent treatment at elevated temperature, e.g. thermofixing at 180° to 210° C. Cellulose $2\frac{1}{2}$ acetate fibres are dyed preferably at temperatures of 80° to 85° C., whereas cellulose triacetate fibres are dyed advantageously at the boiling point of the dye bath. In the dyeing of cellulose $2\frac{1}{2}$ acetate fibres or polyamide fibres, the use of dye carriers is unnecessary. Dyes according to the invention can also be used for printing the said materials by customary methods.

The dyeings obtained by the present process can be subjected to an aftertreatment, for example by being heated with an aqueous solution of an ion-free detergent.

Instead of being applied by impregnation, the given compounds can be applied according to the present process also by printing. For this purpose there is used, for example, a printing ink containing, besides the auxiliaries common in the printing trade, such as wetting and thickening agents, the finely dispersed dye.

Furthermore, it is possible to dye, e.g., synthetic fibres, such as polyesters and polyamides, in organic solvent liquors, such as in a mixture of perchloroethylene and dimethylformamide, or in pure perchloroethylene.

There are obtained by the present process strong brilliant dyeings and printings having excellent fastness properties, especially fastness to light, thermofixing, sublimation, pleating, flue gas, cross-dyeing, dry cleaning, ironing, rubbing, chlorine and wet processing, such as fastness to water, washing and perspiration.

The new water-insoluble dyes can also be used for solution dyeing of polyamides, polyesters and polyolefins. The polymer to be dyed is advantageously mixed in the form of powder, granules or chips, as a finished spinning solution or in the melted state, with the dye, which is introduced in the dry state or in the form of a dispersion or solution in an optionally volatile solvent. After homogeneous dispersion of the dye in the solution or melt of the polymer, the mixture is processed in a known manner by casting, moulding or extrusion into the form of fibres, yarns, monofiliments, films, etc.

The dyes according to the invention are excellently suitable for the dyeing of macromolecular materials such as lacquers, films, sheets and moulded articles, for example those made from cellulose esters such as cellulose 2½ acetate and cellulose triacetate, polyvinyl compounds such as polyvinyl chloride or polyvinyl acetate; polyurethanes, polystyrene, polyesters, polyamides and polycarbonates in the mass.

The basic dyes or dye salts having an optionally quaternised amino, hydrazino or etherified hydroxylamino group or nitrogen-containing heterocyclic groups, obtained according to the invention, are suitable for dyeing and printing the widest variety of fully-synthetic fibres, such as polyvinyl chloride, polyamide or polyurethane fibres, also fibres from polyesters of aromatic dicarboxylic acids, e.g. polyethylene terephthalate fibres and anionically modified polyester and polyamide fibres, especially however also polyacrylonitrile fibre materials or polyvinylidene cyanide fibres (Darvan). By polyacrylonitrile fibres are meant, in particular, polymers which contain more than 80%, e.g. 80 to 95%, of acrylonitrile; in addition they contain 5 to 20% of vinyl acetate, vinyl pyridine, vinyl chloride, vinylidene chloride, acrylic acid, acrylic acid ester, methacrylic acid, methacrylic acid ester, etc. These products are sold for example under the following trade-names: "Acrilan 1656" (The Chemstrand Corporation, Decatur, Alabama, USA), "Acrilan 41" (The Chemstrand Corporation), "Creslan" (American Cyanamide Company), "Orlon 44" (Du Pont), "Crylor HH" (Soc. Rhodiaceta SA, France), "Leacril N" (Applicazioni Chimice Società per Azioni, Italy), "Dynel" (Union Carbide Chem. Corp.), "Exlan" (Japan Exlan Industry Co., Japan), "Vonnel" (Mitsubishi, Japan), "Verel" (Tennessee Eastman, USA), "Zefran" (Dow Chemical, USA), "Wolcrylon" (Filmfabrik Agfa, Wolfen), "Ssaniw" (U.S.S.R.) and also "Orlon 42", "Dralon", "Courtelle", etc.

On these fibres, which can also be dyed in admixture with each other, there are obtained with the new dyes intense and level dyeings having good fastness to light and good general fastness properties, particularly good fastness to washing, perspiration, sublimation, creasing, decatising, ironing, rubbing, carbonising, water, chlorinated water, sea water, dry cleaning, cross-dyeing and solvents. The new dyes according to the invention have, inter alia, a good stability in an extensive pH range, a good affinity, e.g. in aqueous solutions of various pH values, and fastness to kier-boiling. A further advantage is the good reserve on wool and on other natural polyamide fibres, and also on cotton. The dyeings are distinguished by brilliant shades.

The quaternised, water-soluble dyes are in general less electrolyte-sensitive, and have in part a markedly good solubility in water or in polar solvents. The dyeing with the quaternised, water-soluble dyes is generally performed in an aqueous, neutral or acid medium, at the boiling temperature under atmospheric pressure, or in a closed vessel at elevated temperature and under elevated pressure.

They can also be applied by printing to the fibre materials. For this purpose there is used for example a printing paste which contains the dye together with the auxiliaries customary in the printing trade. They are also suitable for the melt dyeing of polymerisation products of acrylonitrile, and also of other plastic, optionally dissolved, masses, in shades fast to light and washing; also for the dyeing of oil paints or lacquers; or finally also for the dyeing of paper and of mordanted cotton.

Except where otherwise stated in the following Examples, parts' are given as parts by weight, percentages as per cent by weight and temperatures in degrees Centigrade. Between parts by weight and parts by volume there exists the same relationship as between gram and cubic centimeter.

Production of the starting products (a) 15.6 parts by weight of o-xylylenedicyanide and 8.5 parts by weight of glyoxal hydrate (trimer) (3 $C_2H_2O_2.2\ H_2O$) having a content of glyoxal to be released of 80% are stirred together in 200 parts by volume of methanol. To the reaction mixture is added portionwise at 15°, with stirring and under nitrogen, 11.2 parts by weight of powdered potassium hydroxide. After the addition of potassium hydroxide, the reaction mixture is further stirred for 15 hours at room temperature under nitrogen. The slightly brown-coloured reaction mixture is subsequently freed in vacuo from the methanol and diluted with 500 parts by volume of water. The precipitated crude 1,4-dicyanonaphthalene is filtered off under suction and washed neutral with water. There are obtained 11 parts by weight of 1,4-dicyannonaphthalene (61.8% of theory) as slightly brown-coloured small needles having a melting point of 175° to 185° C.

After recrystallisation once from alcohol with the aid of 5 parts by weight of active charcoal, there are obtained 5.5 parts by weight of the compound

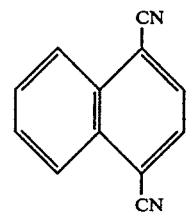

in the form of beautiful needles having a melting point of 204° to 205° C.

(b) 46.4 g of commercial naphthalene-1,4-dicarboxylic acid (content 93%) is introduced with stirring, at a temperature of 20° to 25°, into a flask, fitted with stirrer, containing 480 g of 93% sulphuric acid. The thick suspension obtained is cooled to 0° and an addition is made dropwise at 0° to 2° in the course of 30 minutes, with external cooling, of a mixture consisting of 22 g of 63% nitric acid and 22 g of 93% sulphuric acid. Stirring is maintained at 0° to 5° for a further 5 hours and the mixture is subsequently poured onto 1 kg of fine ice. The precipitated product is filtered off on a suction filter and washed with water until neutral, whereupon the resulting product of the formula

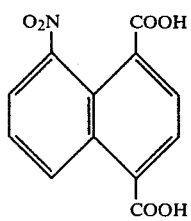

is dried in vacuo at 70°; yield 45 g.

For purification, 45 g of crude product is briefly heated to boiling with 225 ml of glacial acetic acid; the mixture is allowed to cool and the precipitated product is filtered off at room temperature. In this manner is obtained the nitro compound as light-grey powder, which completely dissolves in water with the addition of sodium carbonate; melting point 252°.

(c) 52 parts of 8-nitro-naphthalene-1,4-dicarboxylic acid are dissolved in 700 parts of absolute ethyl alcohol, and the solution is refluxed for 12 hours with the continuous introduction of hydrochloric acid gas. The solution obtained is concentrated in vacuo. The 8-nitro-naphthalene-1-carboxylic acid-4-carboxylic acid ethyl ester of the formula

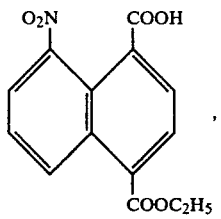

obtained in this manner, melts at 178° to 180°.

If the monoester is hydrogenated, the above-described 1,8-naphtholactam-4-carboxylic acid ethyl ester is obtained, which proves that the esterification of the carboxylic acid group in the 4-position has occured.

(d) 130 parts of 8-nitro-naphthalene-1,4-dicarboxylic acid are dissolved in 500 parts of dimethylformamide; 40 parts of sodium hydroxide are added and, after 30 minutes' stirring, 170 parts by volume of diethylsulphate are added all at once. The temperature rises thereupon to 90°. Stirring is maintained for two hours without regard to the temperature; the solution is then filtered off from the small amount of impurities and poured into 2500 parts by volume of a 10% sodium chloride solution and 50 parts by volume of a 30% sodium hydroxide solution. After a short stirring, the 8-nitro-naphthalene-1,4-dicarboxylic acid diethyl ester, m.p. 107° to 109°, is filtered off with suction, washed and dried.

(e) 32 parts of 8-nitro-naphthalene-1,4-dicarboxylic acid diethyl ester are stirred into 200 parts of glacial acetic acid and, after the addition of 20 parts of iron powder, refluxing is performed for 6 hours. In further processing, the reaction mixture is filtered hot, the filtrate is diluted with the same volume of water, and the thus precipitated 1,8-naphtholactam-4-carboxylic acid ethyl ester is filtered off, washed until neutral and dried. The product of the formula

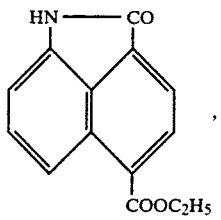

obtained in good yield, melts at 216° to 218°. The analysis gives the following values:

|  | C | H | N |
|---|---|---|---|
| calculated: | 69.7 | 4.6 | 5.8 |
| found: | 69.3 | 4.5 | 5.6 |

(f) 29 parts of 8-nitro-naphthalene-1,4-dicarboxylic acid dimethyl ester (obtainable analogously to Example 5 with dimethylsulphate) are dissolved in 500 parts of ethyl acetate and hydrogenated with Raney nickel. The 8-amino-1-naphtholactam-4-carboxylic acid methyl ester thereupon precipitates out almost completely. After completed hydrogenation, filtration is performed and the residue is extracted with methyl glycol. On concentration by evaporation of the extraction solution there is obtained the ester of the formula

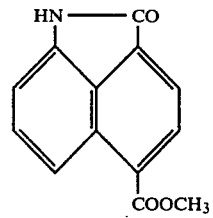

having a melting point of 264° to 266°. The analysis gives the following values:

|  | C | H | N |
|---|---|---|---|
| calculated: | 68.72 | 3.99 | 6.17 |
| found: | 68.5 | 4.0 | 5.9 |

(g) 24 parts of 8-amino-1-naphtholactam-4-carboxylic acid ethyl ester are refluxed for one hour in 180 parts of water and 20 parts of a 30% sodium hydroxide solution, with a complete solution resulting. This is filtered whilst still hot with charcoal and the filtrate is acidified. The 8-amino-1-naphtholactam-4-carboxylic acid which has precipitated is filtered off after cooling, washed with water and dried.

EXAMPLE 1

To a mixture consisting of 12.75 g of naphtholactam-5-carboxylic acid, 10.50 g of benzthiazolyl-acetonitrile and 90 ml of chlorobenzene is added dropwise at a temperature of 100°, within 30 minutes, a mixture of 18.90 ml of phosphorus oxychloride and 18 ml of chlorobenzene, whereupon the mixture is stirred for a further 3 hours at the same temperature. It is then allowed to cool; the formed product is isolated by filtration and is repeatedly washed with chlorobenzene in small portions. There is thus obtained a dye acid chloride of the formula

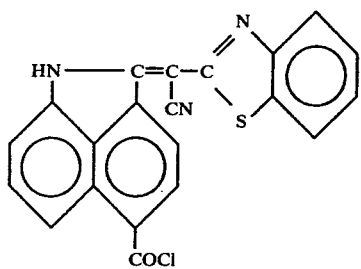

which can be used directly for further reactions.

If there are used, instead of benzthiazolyl-acetonitrile, equivalent amounts of the methylene-active compounds listed in the following Table under I, with otherwise the same procedure, there are obtained the dye acid chlorides given under II of the said Table.

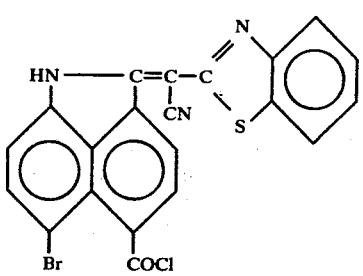

EXAMPLE 2

A mixture consisting of 7.8 g of dye acid chloride of the formula

| No. | I<br>Methylene-active compounds | II<br>Dye acid chlorides |
|---|---|---|
| 1 | (benzoxazolyl)—C—CH₂—CN | (naphthostyryl)—HN—C=C(CN)—C—(benzoxazolyl), COCl |
| 2 | H₃C-(benzoxazolyl)—C—CH₂—CN | HN—C=C(CN)—C—(benzoxazolyl-CH₃), COCl |
| 3 | Cl-(benzoxazolyl)—C—CH₂—CN | HN—C=C(CN)—C—(benzoxazolyl-Cl), COCl |
| 4 | H₃C-(benzoxazolyl with CH₃)—C—CH₂—CN | HN—C=C(CN)—C—(benzoxazolyl with CH₃ and CH₃), COCl |
| 5 | (benzimidazolyl-NH)—C—CH₂—CN | HN—C=C(CN)—C—(benzimidazolyl-NH), COCl |

If an equivalent amount of 4-bromonaphthostyryl-5-carboxylic acid is used instead of naphthostyryl-5-carboxylic acid, with otherwise the same procedure, there is obtained the dye acid chloride of the formula

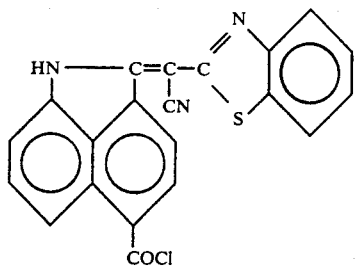

(as suction-filter residue moist with chlorobenzene), 8.20 g of dimethylamino-propylenediamine and 25 ml of chlorobenzene is stirred for 3 hours at a temperature of 110°; it is then allowed to cool; the formed precipitate is filtered off, washed with chlorobenzene, then with methanol and finally with water. The resulting dye of the formula

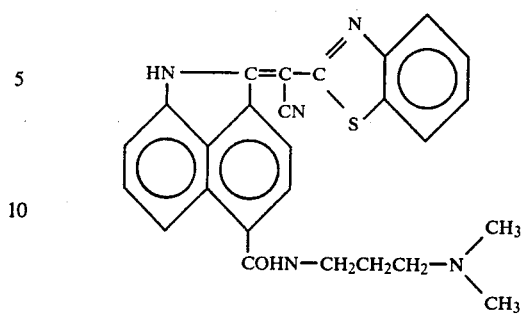

is dried at 70° in vacuo. The dye produces on polyacrylonitrile fabric, applied from a weakly acid bath, brilliant scarlet dyeings which are distinguished by good fastness properties.

If there are used equivalent amounts of the dye acid chlorides listed under I in the following Table and of the amino compounds given under II, with otherwise the same procedure, there are obtained the dyes shown in column III, which likewise dye polyacrylonitrile in a fast shade of colour.

| No. | I Dye acid chlorides | II Amino compounds | III Dyes | IV Shade on PAC |
|---|---|---|---|---|
| 1 | (structure) | $H_2N-CH_2CH_2-N(CH_3)_2$ | (structure) | red |
| 2 | " | $H_2N-N(CH_3)_2$ | (structure) | " |
| 3 | " | $HO-CH_2CH_2-N(CH_3)_2$ | (structure) | " |
| 4 | " | $H_2N-C_6H_4-CH_2-N(CH_3)_2$ | (structure) | " |

-continued
| No. | I Dye acid chlorides | II Amino compounds | III Dyes | IV Shade on PAC |
|---|---|---|---|---|
| 5 | " | 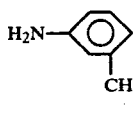 | 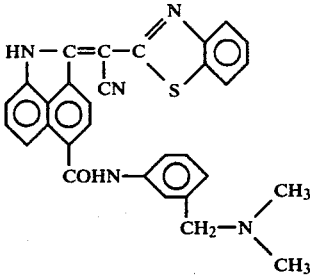 | " |
| 6 | " | 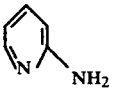 | 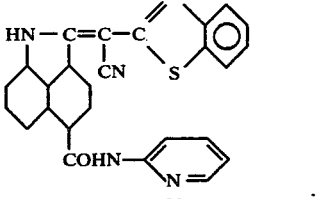 | " |
| 7 | " | 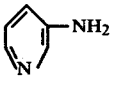 | 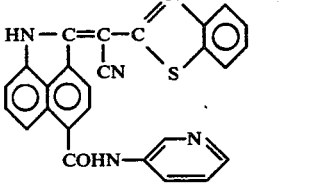 | " |
| 8 | " |  | 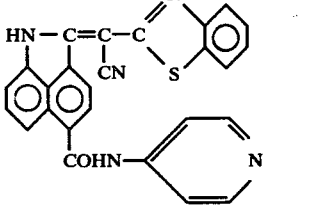 | " |
| 9 | " |  | 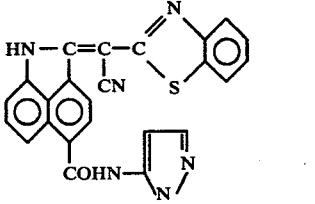 | " |
| 10 | " | 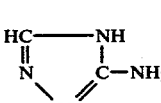 | 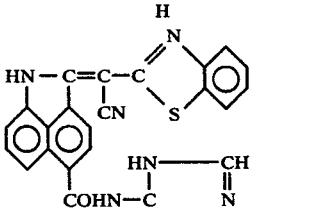 | " |
| 11 | 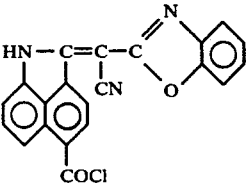 | 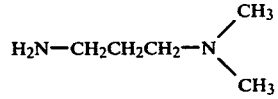 | 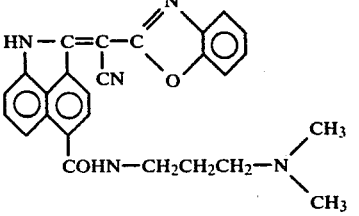 | " |

-continued

| No. | I Dye acid chlorides | II Amino compounds | III Dyes | IV Shade on PAC |
|---|---|---|---|---|
| 12 | " | H₂N—CH₂CH₂—N(CH₃)₂ | [dye structure] | " |
| 13 | " | H₂N—C₆H₄—CH₂—N(CH₃)₂ | [dye structure] | " |
| 14 | " | 2-aminopyridine | [dye structure] | " |
| 15 | " | 3-amino-1,2,4-triazole | [dye structure] | " |
| 16 | [acid chloride with CH₃-benzoxazole] | H₂N—CH₂CH₂CH₂—N(CH₃)₂ | [dye structure] | " |
| 17 | " | H₂N—CH₂CH₂—N(CH₃)₂ | [dye structure] | " |
| 18 | " | H₂N—C₆H₄—CH₂—N(CH₃)₂ | [dye structure] | " |

-continued

| No. | I<br>Dye acid chlorides | II<br>Amino compounds | III<br>Dyes | IV<br>Shade on PAC |
|---|---|---|---|---|
| 19 | " | 2-aminopyridine | dye structure with pyridyl amide | " |
| 20 | " | 3-amino-1,2,4-triazole | dye structure with triazolyl amide | " |
| 21 | chloro-benzoxazole naphthalene COCl | H₂N—CH₂CH₂CH₂—N(CH₃)₂ | dye with dimethylaminopropyl amide | " |
| 22 | " | H₂N—CH₂CH₂—N(CH₃)₂ | dye with dimethylaminoethyl amide | " |
| 23 | " | H₂N—C₆H₄—CH₂—N(CH₃)₂ | dye with (dimethylaminomethyl)phenyl amide | " |
| 24 | " | 2-aminopyridine | dye with pyridyl amide, Cl-substituted | " |
| 25 | " | 3-amino-1,2,4-triazole | dye with triazolyl amide, Cl-substituted | " |

-continued

| No. | I Dye acid chlorides | II Amino compounds | III Dyes | IV Shade on PAC |
|---|---|---|---|---|
| 26 | naphthalene with HN—C=C(CN)— linked to 5,7-dimethylbenzoxazole; COCl substituent | H₂N—CH₂CH₂CH₂—N(CH₃)₂ | corresponding dye: COHN—CH₂CH₂CH₂—N(CH₃)₂ | " |
| 27 | " | H₂N—CH₂CH₂—N(CH₃)₂ | corresponding dye with COHN—CH₂CH₂—N(CH₃)₂ | " |
| 28 | naphthalene with HN—C=C(CN)— linked to benzimidazole (NH); COCl substituent | " | corresponding dye with COHN—CH₂CH₂—N(CH₃)₂ | " |
| 29 | naphthalene with HN—C=C(CN)— linked to hexahydrobenzimidazole (NH); COCl substituent | H₂N—CH₂CH₂CH₂—N(CH₃)₂ | corresponding dye with COHN—CH₂CH₂CH₂—N(CH₃)₂ | " |
| 30 | naphthalene with HN—C=C(CN)— linked to hexahydrobenzothiazole; Br, COCl substituents | H₂N—CH₂CH₂—N(CH₃)₂ | corresponding dye: Br, COHN—COHN—CH₂CH₂—N(CH₃)₂ | " |
| 31 | " | H₂N—CH₂CH₂CH₂—N(CH₃)₂ | corresponding dye: Br, COHN—CH₂CH₂CH₂—N(CH₃)₂ | " |
| 32 | naphthalene with HN—C=C(CN)— linked to benzothiazole; Br, COCl substituents | H₂N—C₆H₄—CH₂—N(CH₃)₂ | corresponding dye: Br, COHN—C₆H₁₀—CH₂—N(CH₃)₂ | " |

| No. | I Dye acid chlorides | II Amino compounds | III Dyes | IV Shade on PAC |
|-----|----------------------|---------------------|----------|-----------------|
| 33 | " | 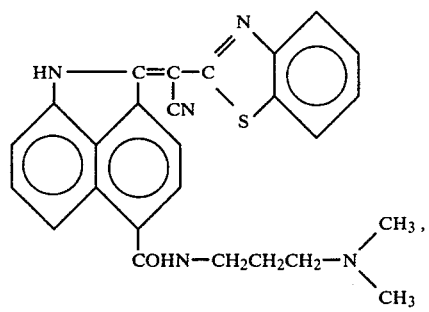 | | " |
| 34 | " | | | " |

EXAMPLE 3

A mixture consisting of 4.55 g of the dye of the formula

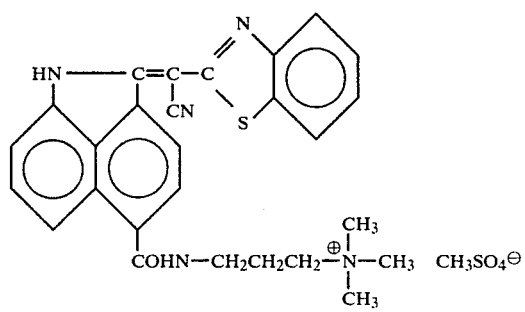

0.20 g of magnesium oxide, 1.65 g of dimethylsulphate and 45 ml of chlorobenzene is mixed for 4 hours at a temperature of 85° to 90°, whereupon the formed dye salt of the formula is isolated at 70° by filtration; it is washed with hot chlorobenzene and then with petroleum ether and subsequently dried at 70° in vacuo. The dye dyes polyacrylonitrile from a weakly acid bath brilliantly red. The dyeings have good fastness properties, particularly a good fastness to decatising.

If instead of the above dye there are quaternised in an analogous manner the dyes of the preceding Table with dimethylsulphate, there are obtained dyes which have similar properties and which dye polyacrylonitrile in a fast red shade.

Dyeing instruction I

One part of the dye obtained according to Example 1 is wet ground with two parts of a 50% aqueous solution of the sodium salt of dinaphthylmethanedisulphonic acid, and the mixture is dried.

This dye preparation is stirred with 40 parts of a 10% aqueous solution of the sodium salt of N-benzylheptadecylbenzimidazoledisulphonic acid, and four parts of a 40% acetic acid solution are added. There is prepared therefrom, by dilution with water, a dye bath of 4000 parts. 100 parts of a cleaned polyester fibre material are introduced into this bath at 50°; the temperature is raised within half an hour to 120° to 130°, and dyeing is performed for one hour in a closed vessel at this temperature. The material is subsequently well rinsed. There is thus obtained a strong red dyeing having excellent fastness to light and to sublimation.

Dyeing instruction II

One part of the dye obtained according to Example 3 is dissolved in 2000 parts of water with the addition of 4 parts of 40% acetic acid, 1 part of crystallised sodium acetate and 10 parts of anhydrous sodium sulphate. Into this dye bath are placed at 60° 100 parts of dried yarn made from polyacrylonitrile staple fibres; the temperature is raised within half an hour to 100° and dyeing is performed for 1 hour at boiling temperature. The scarlet dyeing is subsequently well rinsed and dried.

We claim:
1. Dyes of the formula

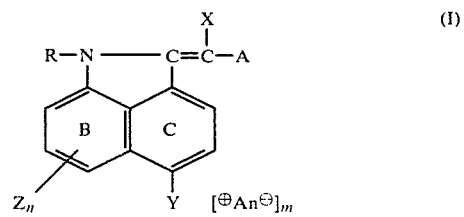

wherein

R represents $C_1$-$C_4$ alkyl, or hydrogen,

X represents CN,

An represents an anion,

Y represents group of the formula

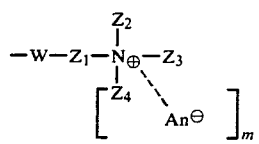

wherein

W represents a group of the formula —CONH—, —COO— or —COS—, $Z_1$ represents alkylene having 1 to 8 C atoms, or $C_2$-$C_6$-alkylene-(O-$C_2$-$C_6$-alkylene)$_{1-3}$, $Z_2$ represents hydrogen, $C_1$-$C_6$ alkyl, or $C_3$-$C_5$-alkenyl, $Z_3$ represents hydrogen, $C_1$-$C_6$ alkyl, or $C_3$-$C_5$-alkenyl, $Z_4$ represents hydrogen, $C_1$-$C_6$ alkyl, $C_3$-$C_5$-alkenyl, cyclohexyl or benzyl, An represents an anion, m represents 0 or 1, Z represents alkyl or alkoxy of 1 to 4 carbon atoms, halogen, alkylmercapto or alkylsulfonyl with 1 to 4 carbon atoms n represents 0, 1 or 2, m represents 0 or 1, and A represents benzthiazole, benzoxazole, benzimidazole optionally substituted by one or two $C_1$-$C_4$-alkyl groups or chlorine or bromine atoms or —CN.

2. Dyes according to claim 1, characterised in that $Z_2$, $Z_3$ and Z represent $C_1$-$C_6$ alkyl, and $Z_1$ is benzyl.

3. A dye of claim 1 having the formula

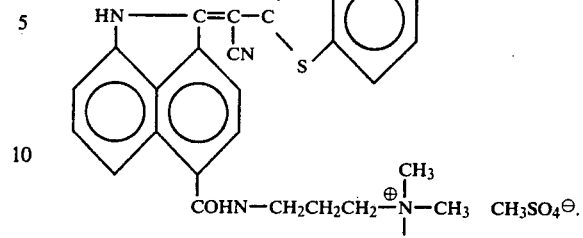

4. A dye of claim 1 having the formula

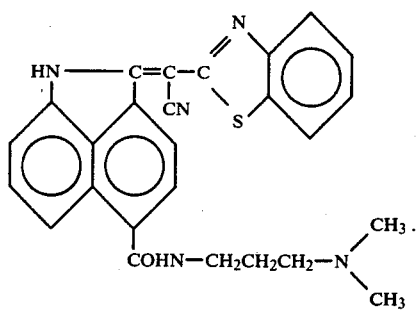

5. A dye of claim 1 having the formula

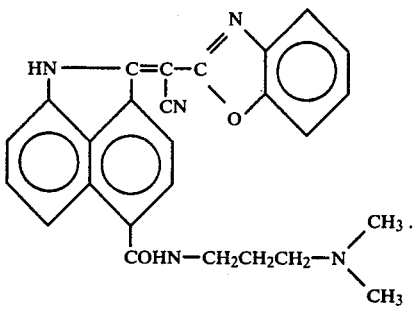

6. A dye of claim 1 having the formula

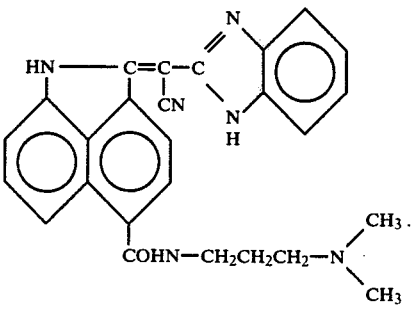

* * * * *